United States Patent [19]

Rembaum

[11] Patent Number: 4,678,814
[45] Date of Patent: Jul. 7, 1987

[54] POLYACROLEIN MICROSPHERES

[75] Inventor: Alan Rembaum, Pasadena, Calif.

[73] Assignee: California Institute of Technology, Pasadena, Calif.

[21] Appl. No.: 750,028

[22] Filed: Jul. 1, 1985

Related U.S. Application Data

[62] Division of Ser. No. 520,313, Aug. 4, 1983, Pat. No. 4,622,362, Division of Ser. No. 248,899, Mar. 30, 1981, Pat. No. 4,413,070.

[51] Int. Cl.$^4$ .......................... C08F 2/54; C08F 16/34
[52] U.S. Cl. ..................................... 522/175; 522/79; 522/81; 522/174
[58] Field of Search ................... 522/175, 174, 79, 81

[56] References Cited

U.S. PATENT DOCUMENTS 4,413,070 11/1983 Rembaum .......................... 523/223
4,622,362 11/1986 Rembaum .......................... 526/315

Primary Examiner—Morton Foelak
Attorney, Agent, or Firm—Marvin E. Jacobs

[57] ABSTRACT

Microspheres of acrolein homopolymers and copolymer with hydrophillic comonomers such as methacrylic acid and/or hydroxyethylmethacrylate are prepared by cobalt gamma irradiation of dilute aqueous solutions of the monomers in presence of suspending agents, especially alkyl sulfates such as sodium dodecyl sulfate. Amine or hydroxyl modification is achieved by forming adducts with diamines or alkanol amines. Carboxyl modification is effected by oxidation with peroxides. Pharmaceuticals or other aldehyde reactive materials can be coupled to the microspheres. The microspheres directly form antibody adducts without agglomeration.

21 Claims, 4 Drawing Figures

POLYACROLEIN MICROSPHERES

ORIGIN OF THE INVENTION

The invention described herein was made in the performance of work under a NASA contract and is subject to the provisions of Section 305 of the National Aeronautics and Space Act of 1958, Public Law 83–568 (72 Stat. 435; 42 USC 2457).

This is a division of application Ser. No. 520,313, filed Aug. 4, 1983 U.S. Pat. No. 4,622,362 which in turn is a division of prior application Ser. No. 248,899, filed Mar. 30, 1981 U.S. Pat. No. 4,413,070.

TECHNICAL FIELD

The present invention relates to the synthesis of polyacrolein microspheres, functional derivatives thereof, fluorescent and magnetic variations thereof, protein conjugates thereof and to the use of the conjugates in biological and chemical research and testing.

BACKGROUND OF THE PRIOR ART

The isolation and characterization of cell membranes and their components is essential for an understanding of the role in which surface membranes play in regulating a wide variety of biological and immunological activities. The present techniques used for this purpose are not quite satisfactory.

Knowledge of the nature, number and distribution of specific receptors on cell surfaces is of central importance for an understanding of the molecular basis underlying such biological phenomena as cell-cell recognition in development, cell communication and regulation by hormones and chemical transmitters, and difference in normal and tumor cell surfaces. In previous studies, the localization of antigens and carbohydrate residues on the surface of cells, notably red blood cells and lymphocytes, has been determined by bonding antibodies or lectins to such molecules as ferritin, hemocyanin or peroxidase which have served as markers for transmission electron microscopy. With advances in high resolution scanning electron microscopy (SEM), however, the topographical distribution of molecular receptors on the surfaces of cell and tissue specimens can be readily determined by similar histochemical techniques using newly developed markers resolvable by SEM.

Recently, commercially available polystyrene latex particles have been utilized as immunologic markers for use in the SEM technique. The surface of such polystyrene particles is hydrophobic and hence certain types of macromolecules such as antibodies are absorbed on the surface under carefully controlled conditions. However, such particles stick non-specifically to many surfaces and molecules and this seriously limits their broad application.

The preparation of small, stable spherical Poly-Hema particles which are biocompatible, i.e., do not interact non-specifically with cells or other biological components and which contain functional groups to which specific proteins and other biochemical molecules can be covalently bonded is disclosed in U.S. Pat. No. 3,957,741.

Smaller, more evenly shaped acrylic microspheres are disclosed in U.S. Pat. No. 4,138,383. Microspheres having a density differing from that of cell membranes are disclosed in U.S. Pat. No. 4,035,316 and fluorescentacrylic copolymer microspheres are disclosed in Ser. No. 718,104 filed Aug. 27, 1976.

The hydroxyl groups can be activated by cyanogen bromide for covalent bonding of proteins and other chemicals containing amino groups to the polymeric bead. Methacrylic acid residues which impart a negative charge onto the particles are likely to prevent non-specific binding to cell surfaces and to provide carboxyl groups to which a variety of biochemical molecules can be covalently bonded using the carbodiimide method.

The derivatization procedure is unnecessarily complex and requires an additional step to prepare the bead surface for covalently binding to proteins such as antibodies, lectins and the like or other molecules such as DNA, hormones and the like. Therefore, the method of derivatization of acrylic microbeads is tedious and availability is limited. Monomeric glutaraldehyde has been used as a biochemical reagent to covalently bond proteins such as immunoglobulins to ferritin polymeric microspheres and other small particles which were then utilized to map receptors on cell membranes. However, the reaction mechanism of proteins with glutaraldehyde is difficult to ascertain since its structure is still not clear and it has been reported to be in equilibrium with cyclic and hydrated forms. The reaction is difficult to carry out and frequently gives unsatisfactory results.

Direct protein bonding polyglutaraldehyde or copolymers therefore disclosed in copending application Ser. Nos. 21,988 and 21,989, both filed Mar. 19, 1979 prepared by solution polymerization in aqueous basic medium. In contrast to monomeric glutaraldehyde, the polymers contain conjugated aldehyde groups. This imparts stability to the Schiff's bases formed after reaction with proteins and, further, since the hydrophilic polyglutaraldehyde has relatively long chains extending from the surface into the surrounding aqueous medium, the heterogenous reaction with protein is facilitated.

Polyglutaraldehyde (PGL) microspheres can be directly prepared by suspension polymerization with stirring in presence of surfactant or by precipitation from solution containing surfactant. Magnetic, high density or electron dense microspheres can be prepared by coating metal particles or by suspension polymerization of glutaraldehyde in presence of a suspension of finely divided metal or metal oxide. It has been determined that the PGL microspheres exhibit some degree of non-specific binding to cells. Moreover, though some cross-linking occurs during the homopolymerization of glutaraldehyde, the polymer can be dissolved in highly polar solvents.

A process for polymerizing unsaturated aldehydes such as acrolein is disclosed in U.S. Pat. No. 3,105,801. The process comprises adding a small amount of acid or an acid-acting material to an aqueous solution containing acrolein or other unsaturated aldehyde and exposing the acidic medium to high energy ionizing radiation to form high molecular weight polymer in the form of light powders having non-uniform shapes and sizes. The polymers were not utilized as such but are dissolved in aqueous alkaline sulfur dioxide solution to form water soluble derivatives which are used as coatings or sizings for paper, cloth, fibers and the like. Bell et al also discusses the copolymerization of acrolein with a wide variety of ethylenically unsaturated monomers such as ethylene diamine, pyridine or acrylic acids or esters, vinyl halides, etc. in amounts from 0.1 to 60%, preferably from 1% to 25% by weight of the monomer mixture.

The monomer mixture can contain other agents such as stabilizing, suspending as emulsifying agents. Radiation accelerators such as halides or metal salts may be added to the reaction mixture.

Though the polyacroleins prepared by Bell et al have a high degree of available aldehyde function, there was no recognition of the use of such material as a biological reagent. Furthermore, the presence of extraneous ingredients interferes with the purity of the polymer and it would not be suitable as a biochemical protein bonding agent. Furthermore, specific modification of the material by copolymerization with certain comonomers designed to impart further properties such as non-specific binding and modification to add other functional groups for introduction of dyes, proteins or other materials would improve the flexibility of use of the material.

DESCRIPTION OF THE INVENTION

Novel acrolein interpolymer microspheres and functional, modified reaction products and protein adducts thereof, are produced in accordance with the invention. The size and properties of the microspheres can be controlled by selection of polymerization conditions and especially by selection of comonomers. The microspheres of the invention exhibit exceptional stability and can be derivatized by reaction with amines or with proteins without aggregation.

The non-aggregating microspheres are produced in accordance with this invention by the high-energy initiated interpolymerization of an unsaturated aldehyde such as acrolein and at least 20% by weight of at least one addition copolymerizable comonomer having a hydrophilic functional substituent selected from hydroxyl, amino or carboxyl.

Another manner of introducing functionality other than aldehyde onto the microspheres is by adduct reaction of the microspheres with compounds of the formula:

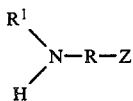

where $R^1$ is hydrogen or a hydrocarbon group which may be aliphatic or aromatic preferably aryl such as phenyl or alkyl of 1 to 10 carbon atoms, R is a divalent hydrocarbon group such as alkylene of 1 to 20 carbon atoms and Z is a functional group such as amine or hydroxyl or RZ can be hydroxyl. Representative compounds are hydroxylamine or ethylene diamine. The microspheres can be modified to introduce carboxyl groups by oxidation with an agent such as hydrogen peroxide.

The microspheres of the invention exhibit little or no aggregation during or after derivatization reaction to introduce large amounts of antibodies or other proteins, fluorochromes, etc. The microspheres are insoluble, have functional groups directly reactive with protein, are easily dispersed and bind specifically to receptor sites and can be readily prepared in sizes from 100 Angstroms to 2,000 Angstroms, or up to 10 microns or larger if desired.

The derivatization procedure is simplified. The hydroxyl modified microspheres can be used to chelate metals as a purification media or as a support for a catalyst. The microspheres can be formed into a strong transparent film by drying on a surface or can be formulated to contain metals which can be utilized to form election dense magnetic non-aggregating particles or magnetic coatings or films. The microspheres of the invention provide a reliable, simple method to label cells for research or analysis.

The microspheres of the invention can also be utilized as a substrate to bind pharmaceuticals containing functional groups reactive with aldehyde, the hydrophillic hydroxyl, carboxyl or amine substituent or the functional group Z of the adduct. The microsphere-pharmaceutical adduct is less likely to migrate and should reduce side effects. Furthermore, antibodies can be attached to the microsphere so that it migrates to specific cells having corresponding antigen receptor sites. Magnetic microspheres can be accumulated at a specific location in a subject by application of a magnetic field to that location.

These and many other features and attendant advantages of the invention will become apparent as the invention becomes better understood by reference to the following detailed description when considered in conjunction with the accompanying drawings.

DETAILED DESCRIPTION OF THE INVENTION

Figure 1:
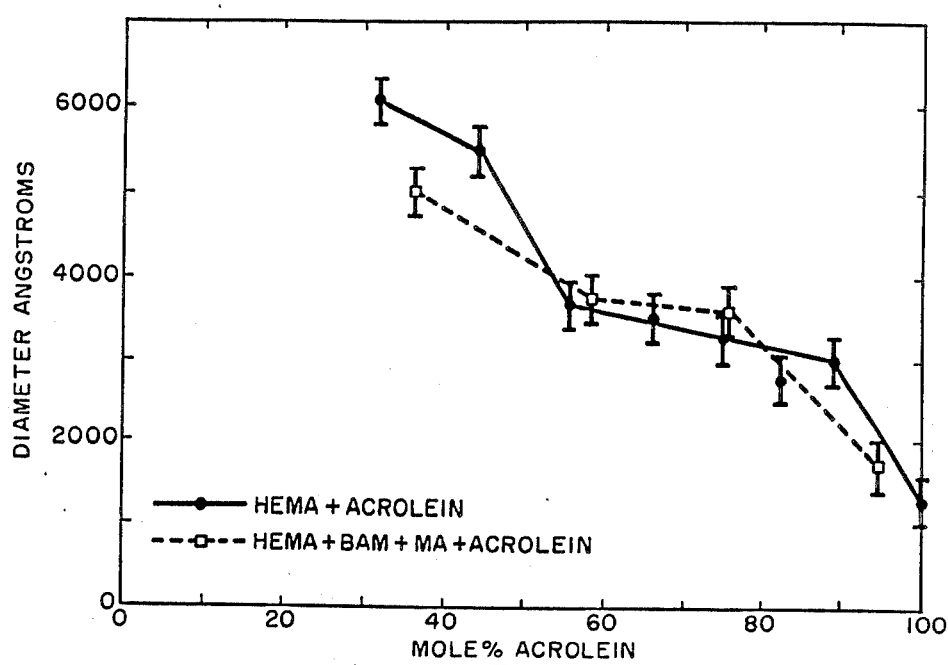
FIG. 1 is a series of graphs showing the effect of addition of comonomers on the size of acrolein copolymer microspheres.

Initiation of copolymerization by high energy radiation in absence of chemical initiators or acid materials provides a purer and more evenly sized and shaped microsphere. The microspheres are produced by addition polymerization of a liquid polymerization system optionally including a dispersion of the metal particles in a monomer mixture containing a covalently bondable unsaturated monomer. More uniformly sized and shaped beads are formed in very dilute aqueous monomer mixtures of no more than 5% by weight, preferably 1 to 4% by weight of dissolved monomers. Surfactants may be present to aid in the dispersion of the metal particles and in suspending the microspheres.

The polymerization proceeds with or without stirring with application of high energy radiation capable of generating free radicals in the aqueous system. The radiation source is suitably a cobalt 60 gamma source or cesium source and doses of 0.05 to 2.0 megarads are sufficient for polymerization. It is believed that polymer chains grow from the surface of metallic particles. The reaction is preferably conducted under oxygen excluding condition, generally by applying vacuum to the reaction vessel or by displacing oxygen gas from the system with an inert gas such as nitrogen. After polymerization has proceeded to completion, the reaction mixture is made neutral by adding acid or base, passed through mixed ion exchange resins to remove emulsifiers or any free metal particles. Further purification is achieved by centrifugation on a sucrose gradient.

The addition of 0.05 to 5%, by weight, of a stabilizing agent to the aqueous polymerization system before polymerization is found to further reduce agglomeration. The stabilizing agent is suitably an aqueous soluble polymer such as a polyalkylene oxide polyether or non-ionic surfactants such as Tween which are polyoxyethylene derivatives of fatty acid partial esters of sorbitol, Triton X, or dextrans. The polyethers generally have a molecular weight from 10,000 to 10,000,000, preferably 400,000 to 6,000,000 and are polymers of ethylene oxide, propylene oxide or their mixtures. Polyethylene oxides (PEO) and Triton X are preferred.

The smaller microspheres (50 to 200 Angstroms in diameter) are formed in solutions containing small amounts, typically from 10 to 150 millimoles, of an alkali metal $C_8$ to $C_{20}$ alkyl sulfate surfactant such as sodium lauryl sulfate (SLS) or sodium dodecyl sulfate (SDS).

The ethylenically unsaturated aldehydes should comprise at least 10% by weight of the monomer mixture preferably from 20% to 90% by weight thereof. The aldehydes preferably have the ethylenic group in alpha-beta position relative to the aldehyde group and can be selected from those aldehydes containing up to 20 carbon atoms such as acrolein, methacrolein, alpha-ethyl acrolein, alpha-butylacrolein, alpha-chloroacrolein, beta-phenylacrolein, alpha-cyclohexyl acrolein and alpha-decylacrolein. Preferred aldehydes contain 4 to 10 carbon atoms and especially acrolein and $C_1$ to $C_8$ aryl alkyl and cycloalkyl substituted derivatives thereof.

The mono-unsaturated covalent-bonding monomers are freely water soluble and should comprise from 10 to 50% of the monomer mixture. These monomers are suitably selected from amino, carboxyl or hydroxyl substituted acrylic monomers. Exemplary monomers are acrylamide (AM), methacrylamide (MAM), acrylic acid, methacrylic acid (MA), dimethylaminomethacrylate or hydroxyl-lower alkyl or amino-lower-alkyl-acrylates such as those of the formula:

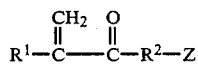

where $R^1$ is hydrogen or lower alkyl of 1-8 carbon atoms, $R^2$ is alkylene of 1-12 carbon atoms, and Z is —OH or $R^3$—N—$R^4$ where $R^3$ or $R^4$ are individually selected from H, lower alkyl or lower alkoxy of 1-8 carbon atoms. 2-hydroxyethyl methacrylate (HEMA), 3-hydroxypropyl methacrylate and 2-aminoethyl methacrylate are readily available commercially. Porosity and hydrophilicity increase with increasing concentration of monomer.

Inclusion of polyunsaturated compounds provides cross-linked beads. The polyunsaturated compounds are generally present in the monomer mixture in an amount from 0.1-20% by weight, generally 6-12% by weight and are suitably a compatible diene or triene polyvinyl compound capable of addition polymerization with the covalent bonding monomer such as ethylene glycol dimethacrylate, trimethylol-propane-trimethacrylate, N,N'-methylene-bis-acrylamide (BAM), hexahydro-1,3,5-triacryloyl-s-triazine or divinyl benzene.

For small particle size and additional reduction in non-specific binding and agglomeration the monomer mixture preferably contains a monomer capable of imparting negative charge such as methacrylic acid (MA).

The mixture may contain 0–40% suitably 10 to 30% of sparingly water soluble monomers having hydrophobic characteristics since this is found to result in freely-suspended, individual, small beads. The cross-linking agent is sometimes sparingly water soluble. Hydrophobic characteristics can also be provided with monomers such as lower alkyl acrylates suitably methyl methacrylate or ethyl methacrylate or a vinyl pyridine. Vinyl pyridines suitable for use in the invention are 2-vinyl pyridine, 4-vinyl pyridine and 2-methyl-5-vinyl pyridine.

Small microspheres (of the order of 100 to 500 Angstroms) containing electron-dense metals provide higher spatial resolution of cell surface features. Immunomicrospheres containing electron-dense metals provide more stable labels than gold particles with physically absorbed antibodies that are presently used for cell labeling. The metal containing microspheres can be synthesized by, in situ, polymerization of the microspheres in presence of a suspension of finely-divided metal particles or compounds of the metal, preferably a colloidal dispersion of the metal. The metal is incorporated into the microsphere in an effective amount of from 0.5% to 40% by weight, generally from 5% to 25% by weight.

The metal or metal compound particles are preferably fine, evenly sized materials having a uniform diameter smaller than the resultant microsphere diameter, typically below 1000Å, generally from 25Å to 500Å. The metals are preferably the electron-dense heavy metals having a high atomic number above 50, preferably above 75 such as Pb, Ni, Co, Pt, Au, Fe. The metal may be magnetically attractable such as Fe, Ni, Co or alloys thereof or an inorganic magnetic compound such as a metal oxide. The magnetic material is preferably a magnetic iron oxide of the formula $Fe_3O_4$. Some hard, ceramic type ferrites, such as lithium ferrites can also be used. The metal or compound can be made into a readily dispersible form by suspension in water containing a surfactant such as polyethylene imine.

Post polymerization reaction with specific fluorocrome reagents that are not in themselves fluorescent, results in a fluorescent microsphere by forming fluorescent chromophores attached to the polymer. Anthrone reacts with acrolein units to form a benzanthrone fluorogen and m-aminophenol reacts with the acrolein structure to form the fluorogen, 7-hydroxyquinoline. Aminofluorescein also reacts with aldehyde groups to form fluorescent microspheres.

The microspheres can also be rendered fluorescent during polymerization in presence of fluorochrome compounds containing aldehyde or hydroxyl reactive groups such as aminofluorescein, 9-amino acridine, propidium bromide or fluorescein isothiocyanate (FITC). Highly fluorescent microspheres can also be prepared by suspension polymerization in presence of fluorochromes containing unsaturated groups capable of reaction with acrolein. Examples of practice follow:

Reagents

Methacrylic acid (MA), 2-hydroxyethyl methacrylate (HEMA), acrolein, ethylene diamine were fractionally distilled. Polyethylene oxide (PEO, $M_w$ 100000) N,N'-methylene-bis-acrylamide (BAM), hydroxylamine hydrochloride, 1,6-hexane diamine, 1.Lysine, 1-ethyl-3-(3-dimethyl amino propyl) carbodiimide were used as received.

Synthesis

Acrolein or monomer mixtures consisting of HEMA and acrolein or HEMA, BAM, MA and acrolein formed homogeneous solutions in distilled water containing 0.4% PEO or 64 mM of SDS. After dearation with nitrogen the mixtures were irradiated in CO gamma source at room temperature (dose rate 0.12 Mr/hour) for 4 hours. The reaction product was purified by three centrifugations and kept in distilled water.

Methods

The aldehyde content was determined from the percent nitrogen of the oxime prepared by the reaction of an aqueous suspension with hydroxylamine hydrochloride [P.J. Bochert Kunstoffe 51 (3) 137 (1961)]. IR spectra were obtained with a Fourrier transform IR (fts-15C, Houston Instruments) spectrophotometer.

EXAMPLE 1

Pure acrolein (5% v/v) in water containing PEO produced colloidal particles (approximately 1,000 Angstroms in diameter) after cobalt gamma irradiation. Repeat of the procedure substituting 64 mM SDS for PEO resulted in 170 Angstrom microspheres in higher yield.

EXAMPLE 2

Acrolein - HEMA copolymer microspheres of eight different HEMA contents were prepared by cobalt gamma irradiation of a 5% (v/v) monomer solution in water containing 0.4% PEO. The diameter of the resulting microspheres decreased with increasing acrolein content as shown in FIG. 1. Over the middle of the concentration range studied, monomer ratios had little effect on size; permitting the preparation of microspheres of similar size but different degrees of hydrophobicity.

When the acrolein homopolymer microsphere suspension was evaporated to dryness, a brittle film was formed. However, evaporation of the HEMA - copolymer (35 mol percent HEMA) microsphere suspension to dryness results in a strong, flexible film.

EXAMPLE 3

Seven of the copolymers were reacted with hydroxylamine chloride to form hydroxyl functional microspheres. The aldehyde content was analyzed by this procedure as shown in Table I.

TABLE 1
HEMA ACROLEIN MICROSPHERES
Determination of aldehyde functional groups by reaction with hydroxylamine hydrochloride

| % (v/v) Acrolein of Total Monomer | Mole % Acrolein[a] | % Yield | Microspheres/mg[b] $\times 10^{-10}$ | % Nitrogen Found[c] | Number of Aldehyde Groups per mg $\times 10^{-18}$ | Number of Aldehyde Groups per microsphere $\times 10^{-7}$ |
|---|---|---|---|---|---|---|
| 30 | 44 | 61.1 | 0.84 | 3.06 | 1.4 | 17.0 |
| 40 | 55 | 50.0 | 3.1 | 4.02 | 1.8 | 5.8 |
| 50 | 65 | 47.9 | 3.7 | 4.84 | 2.2 | 5.9 |
| 60 | 74 | 37.8 | 4.6 | 5.59 | 2.5 | 5.4 |
| 70 | 82 | 36.3 | 6.5 | 6.57 | 3.0 | 7.6 |
| 80 | 88 | 21.6 | 5.2 | 8.58 | 4.0 | 7.8 |
| 100 | 100 | 17.6 | 6.4 | 13.06 | 6.4 | 10.0 |

[a]Mole % of acrolein in monomer mixture.
[b]Calculated using spherical microspheres of diameter shown in FIG. 1 and a density of 1.2 g/ml.
[c]Theoretical nitrogen for homopolymer is 19.72%.

Figure 2:
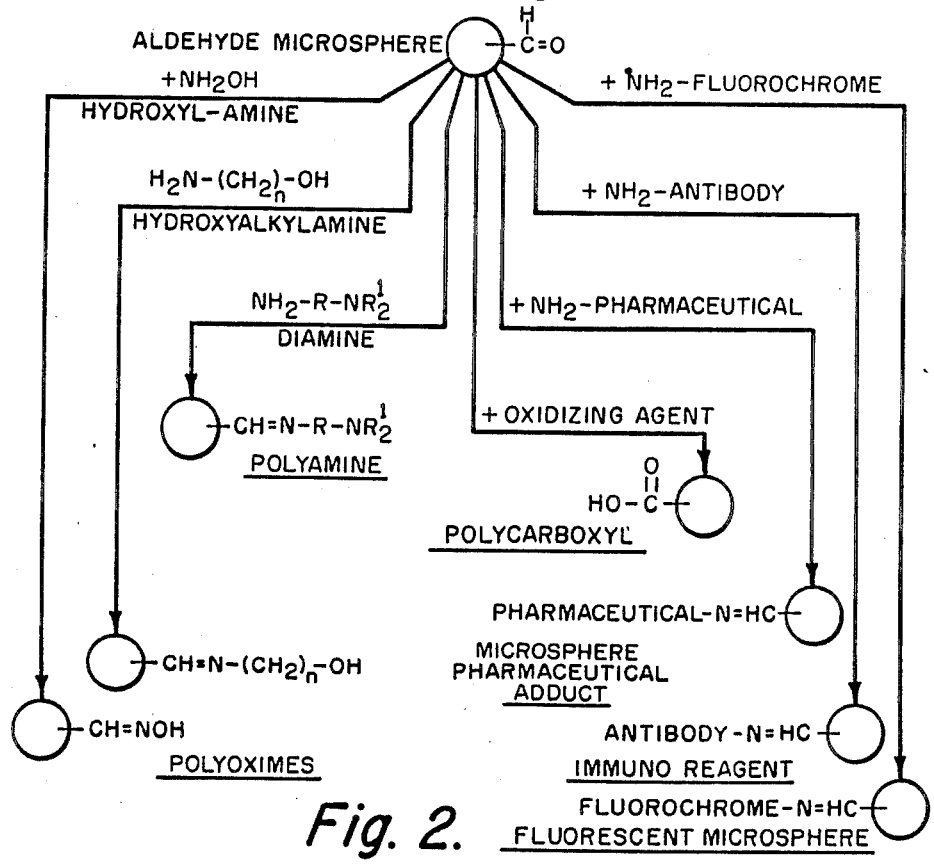
FIG. 2 is a series of schematic reactions of polyacrolein microspheres and various modifying and adducting reagents.

The acrolein homopolymer (100% acrolein) was found to contain approximately 65% of the expected aldehyde groups. The presence of aldehyde groups was further confirmed by IR spectra analysis which showed a high intensity peak at 1725 $cm^{-1}$. Adducts and reaction products are depicted in FIG. 2.

EXAMPLE 4

The hydroxylamine modified copolymer microspheres containing 35% mol HEMA were impregnated with an aqueous solution of copper salt. The copper ions reacted with the microspheres to form metal chelate adducts.

EXAMPLE 5

Cross-linked microspheres containing acid functions were produced by adding MA and BAM to the HEMA - Acrolein monomer mixture. The porosity of the microsphere was significantly increased as evidenced by swelling (uptake of liquid). However, the size of the cross-linked microspheres closely approximated that of the HEMA - ACROLEIN microspheres of Example 2 as shown in FIG. 1. By addition of increasing amounts of BAM to acrolein the hydrophilicity of acrolein spheres could be progressively increased.

EXAMPLE 6

One of the BAM-MA-HEMA-Acrolein copolymers was reacted with various diamine to form amine-modified adducts. The results are shown in Table 2.

TABLE 2
REACTION OF POLY ACROLEIN MICROSPHERES WITH DIAMINES[a]

| Reactant | pH | % Nitrogen | Number of Free Amino Groups per mg | Number of Free Amino Groups per microsphere | pH | % Nitrogen | No. of Free Amino Groups per mg | No. of Free Amino Groups per microsphere |
|---|---|---|---|---|---|---|---|---|
| 1,2 diaminoethane | 3.0 | 1.43 | $3.2 \times 10^{17}$ | $2.4 \times 10^7$ | 11.3 | 4.88 | $1.2 \times 10^{18}$ | $9.2 \times 10^7$ |
| 1,2 diaminohexane | 3.0 | 0.78 | $8.6 \times 10^{16}$ | $6.6 \times 10^6$ | 11.7 | 3.11 | $8.2 \times 10^{17}$ | $6.3 \times 10^7$ |
| L-Lysine | 3.2 | 0.40 | $8.8 \times 10^{16}$ | $6.8 \times 10^6$ | 9.0 | 2.41 | $5.9 \times 10^{17}$ | $4.5 \times 10^7$ |

[a]Reaction mixture for microsphere synthesis; 35.9 mole % acrolein, 56.9 mole % HEMA, 5.9 mole % methacrylic acid 1.3 mole % bisacrylamide.

It was found that at high pH the number of free amino groups was comparable to the number of aldehyde groups found by hydroxylamine analysis. This reaction allows the efficient conversion of aldehyde functions to amine functions, removed from the surface of the spheres by a two to six carbon spacer arm.

The monomer mixture utilized in the experiment in Table 2 was modified by maintaining the ratio of HEMA, MA and BAM constant while adding increasing amounts of acrolein. As shown in Table 3 which follows, the aldehyde content increased with increasing acrolein content proving that acrolein was being incorporated into the copolymer.

TABLE 3

| MOLE % ACROLEIN | % N | No. ALDEHYDE GROUPS/mg $\times 10^{-18}$ |
|---|---|---|
| 35.9 | 3.26 | 1.35 |
| 58.5 | 4.32 | 1.93 |
| 75.8 | 6.57 | 2.90 |
| 95.3 | 12.16 | 5.83 |

EXAMPLE 7

The copolymer of Example 6 was reacted with an adduct of fluorescein isothiocyanate (FITC) and 1,6-diamino-n-hexane which resulted in microspheres of high fluorescent intensity.

EXAMPLE 8

An allyl amine adduct of FITC was prepared. Addition of 0.1% by weight of the adduct to the polymerization system of Example 6 resulted in an addition interpolymerized fluorescent copolymer microsphere.

EXAMPLE 9

An adduct of 1,6-diaminohexane (DAH) and FITC was prepared. Addition of 0.1% of the adduct to the polyerization system of Example 6 resulted in introduction of fluorescent chromophore by condensation with aldehyde groups to the addition polymerized copolymer.

EXAMPLE 10

Dispersible iron oxide was prepared by dissolving 10 g of ferrous chloride and 13.5 g of ferric chloride in 210 cc of 1% w/v polyethylene imine (M.W. 1800) aqueous solution. 50% NaOH was added to pH 7. The reaction mixture was refluxed for 3 hours, dialyzed extensively against water and separated magnetically three times from non-magnetic particles. The magnetic polyethylene imine-iron oxide particles were redispersed in water and then sonicated with a clinical sonicator for 10 minutes. Magnetic particles having a diameter of 300 Angstroms with amine groups on the surface were formed. When 1% of the polyethylene imine-iron oxide is added to the solution of monoers of Example 6 and subjected to gamma irradiation microspheres containing a dispersion of magnetic iron particles is produced.

EXAMPLE 11

Figure 3:
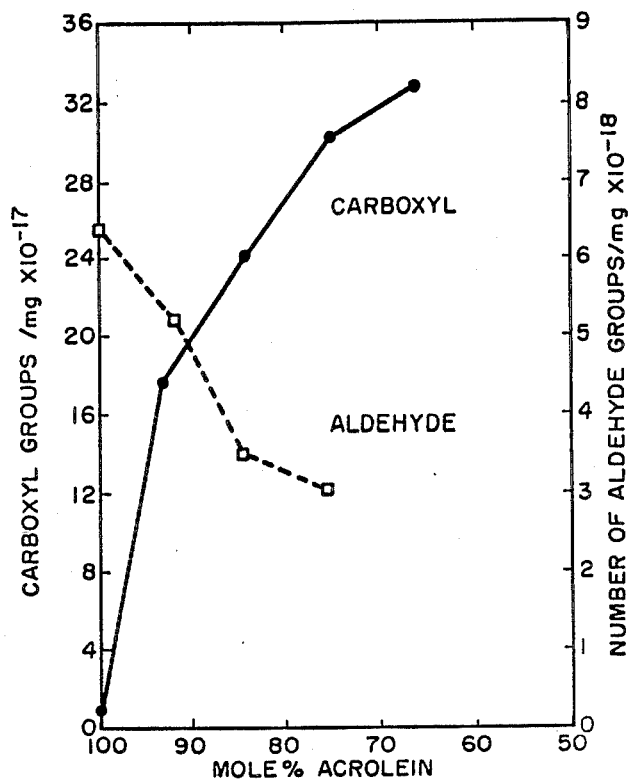
FIG. 3 is a pair of curves illustrating the aldehyde and carboxyl content of oxidized Acrolein-Methacrylic Acid copolymer microspheres.

The Acrolein methacrylic acid copolymer microspheres were oxidized to convert the aldehyde groups to carboxyl adding 30.5 ml $H_2O$ and 90 ml of $H_2O_2$ (30%) to 14.5 ml of an acrolein microsphere suspension (33 mg/ml). The suspension was stirred by a magnetic stirrer for 20 hours. The microspheres were then washed three times and then centrifuged for 15 minutes in water. The results are shown in FIG. 3.

EXAMPLE 12

2 mg of SDS powder was added to 10 cc of 5% (v/v) ACR solution and irradiated for 4 hours with a cobalt gamma source at 0.12 Mr/h and centrifuged 3 times. The particles were not visible. Their size as determined under an electron microscope was about 300–500 Angstroms.

When the SDS content was increased to 50 mg, the particles were too small to be centrifuged. After dialyzing for several days their size as determined by SEM was about 170 to 340 Angstroms.

The marking of cell surface receptors by means of fluorescent, non-fluorescent or magnetic fluorescent PGL microspheres was found to be simple and efficient as evidenced by numerous tests using fixed human or animal antibody labeled cells.

The reactivity is similar to polyglutaraldehyde microspheres. However, no significant aggregation was observed during reactions with amines, diamines or proteins under a variety of experimental conditions. The microspheres are preferably very small in size from 100 Angstroms to 100 microns, generally from 500 Angstroms to 10 microns so that specific receptor sites on a cell surface can be tagged.

EXAMPLE 13

To 2.5 ml of a water suspension of acrolein microspheres (total 15 mg) was added 0.5 of a 2 mg 1 ml solution of 125 Iodine labeled goat immunoglobulin G (spec. activity $1 \times 10^5$ cpm/mg) in PBS. The mixture was rotated for 3 hrs. and 400 microliters aliquots were taken at 0,30,60,120 and 180 minutes. Aliquot were immediately added to 400 ml of a 1% (w/v) solution of egg albumin in PBS and centrifuged at $15,000 \times g$ for 4 min., resuspended and washed once in PBS as above.

Figure 4:
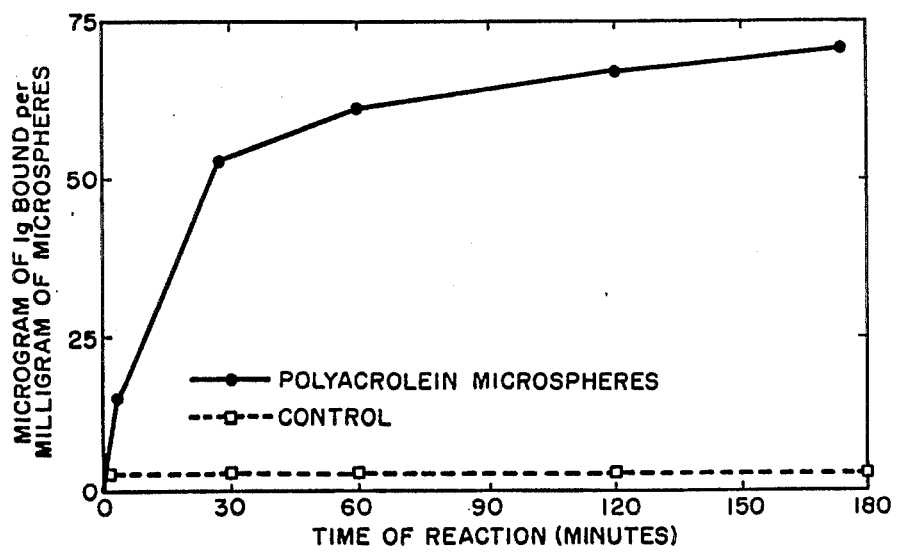
FIG. 4 is a pair of curves demonstrating the kinetics of reaction of polyacrolein microspheres with an antibody.

The acrolein microspheres exhibited direct binding of about 7–9% by weight of antibody whereas a control HEMA-BAM microsphere was able to bind less than 1% by weight of the microsphere. Results are illustrated in FIG. 4.

EXAMPLE 14

Binding of Methotrexate to Polyacrolein Microspheres

I. Preparation of Microspheres
 [10%] - Total monomer concentration
 90% Acrolein
 10% Methacrylic Acid
 in 25 ml 0.4% PEO 100,000 MW
 pH 2.8
 Degas with Nitrogen
 Co Gamma Radiation 5h Dose - 0.12 Mic/hr.
 Wash 3X
 Resuspend 36 ml $H_2O$
  Conc: 27.5 mg/ml
  Yield: 46.13%
II. Reaction of Microspheres with 1-6 Diaminohexane
 50 mg of microspheres
 0.6 ml DAH (8 0% aqueous solution)
 Repeat 4 hr. with shaking at room temperature
 Wash 3×
 Resuspend in 10 ml $H_2O$
III. Reaction of Microspheres with Carbodiimide
 Add 20 mg of carbodiimide to 50 mg of DAH microspheres
 Sonicate 10 minutes
 Adjust pH to 6 w/Na $H_2$ $PO_4$
 Add 10 mg methotrexate in 2 ml $H_2O$
 Check to be sure pH is still 6.0
 Sonicate 2 minutes
 Shake overnight at room temperature Spin down 3×

Take spectrum of first supernate. Spectrum indicates that more than 90% of methotrexate adducted with the microspheres.

A new convenient immunoreagent in form of acrolein copolymer microspheres was synthesized in a variety of sizes and with a relatively narrow size distribution. High intensity of fluorescence can be imparted to the microspheres during or after polymerization. The aldehyde functional groups permit covalent bonding with antibodies, enzymes and other proteins in a single step. Therefore this immunoreagent eliminates the previously used intermediate steps in which the cyanogen bromide and carbodiimide reaction was used. The high specificity of the microspheres, at least as far as human rbc is concerned is also a desirable property. A minor synthetic modification yields fluorescent, magnetic microspheres for a large number of potential applications. The polyacrolein copolymer microspheres of this invention contain approximately twice as many aldehyde groups as the comparable glutaraldehyde copolymer microspheres.

The use of magnetic particles has created a great deal of interest in biochemical research and clinical medicine when used as supports for immobilized enzymes. Their easy retrieval from liquors containing colloids and undissolved solids should be of practical value. The separation of proteins and chemical compounds by affinity chromatography can be simplified by elimination of tedious centrifugation procedures and column chromatography steps. Magnetic particles have also recently been tested in radioimmunoassay techniques in hyperthermia treatment of cancer, in guidance of magnetic particles to a vascular malformation such as cerebral aneurism with the intent to seal the defect by inducing thrombosis.

Other proposed applications have been as tracers of blood flow or vehicles for drug delivery. The first successful application of magnetic immunomicrospheres to the separation of B and T cells has been demonstrated. There is little doubt that physical sorting of cell subpopulations has become a necessity. Many separation methods, while useful are limited by the restricted set of parameters upon which separation can be based and by the fact that they are batch techniques.

New flow cytometers and sorters permit quantitative multiparameter measurements and sorting based on these measurements, but are limited as far as the number of cells that can be separated in a given time. Magnetic cell sorters have the potential of cell separation in a continuous process. Evidence obtained using model cell systems indicates that magnetic immunomicrospheres of desirable sizes can be conjugated with proteins in a simple and convenient manner, therefore offer a potential for large scale immunological cell sorting as well as other applications.

It is to be understood that only preferred embodiments of the invention have been described and that numerous substitutions, modifications and alterations are permissible without departing from the spirit and scope of the invention as defined in the following claims.

I claim:

1. A method of preparing small polymeric microspheres comprising the steps of:
forming a solution of less than 5% by weight of a monomer mixture containing at least 10% by weight of an unsaturated aldehyde selected from the group consisting of acrolein and $C_1$ to $C_8$ aryl, alkyl and cycloalkyl derivatives thereof and at least 20% by weight of at least one addition copolymerizable monomer having a hydrophilic substituent selected from hydroxyl amino or carboxyl and 0.1 to 20% of a polyunsaturated crosslinking agent;
irradiating the solution with radiation capable of initiating polymerization; and
recovering said microspheres.

2. A method according to claim 1 in which the aldehyde is present in the mixture in an amount from 20% to 90% by weight.

3. A method according to claim 1 in which the aldehyde is acrolein.

4. A method according to claim 2 in which the comonomer is present in an amount from 10 to 50% of the mixture and comprises a mono-unsaturated, freely water-soluble acrylic monomer substituted with amino, carboxyl or hydroxyl.

5. A method according to claim 4 in which the comonomer is selected from acrylamide, methacrylamide, acrylic acid, methacrylic acid, dimethylaminomethacrylate or compounds of the formula:

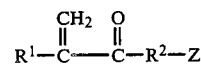

where $R^1$ is hydrogen or lower alkyl of 1-8 carbon atoms $R^2$ is alkylene of 1-12 carbon atoms and Z is —OH or $R^3$-N-$R^4$ where $R^3$ or $R^4$ are individually selected from H, lower alkyl or lower alkoxy of 1-8 carbon atoms.

6. A method according to claim 5 in which the comonomer comprises hydroxyethyl methacrylate.

7. A method according to claim 4 in which the comonomer imparts a negative charge to the microsphere.

8. A method according to claim 7 in which said comonomer is methacrylic acid.

9. A method according to claim 1 in which the crosslinking agent further includes functional groups.

10. A method according to claim 9 in which the cross-linking agent is bis-acrylamide.

11. A method according to claim 2 further including 0.05 to 5% by weight of a copolymerizable fluorescent chromophore monomer.

12. A method according to claim 11 in which the fluorescent monomer contains functional groups reactive with aldehyde.

13. A method according to claim 12 in which the fluorescent monomer contains addition polymerizable unsaturated groups.

14. A method according to claim 2 in which said solution contain a dispersion of metal particles.

15. A method according to claim 14 in which the metals are magnetizable.

16. A method according to claim 1 in which the solution contains a suspending agent.

17. A method according to claim 16 in which the suspending agent is selected from polyalkylene oxide liquid polymers and an alkali metal alkyl sulfate containing 8 to 20 carbon atoms.

18. A method according to claim 17 in which the agent is selected from sodium lauryl sulfate and sodium dodecyl sulfate.

19. A method according to claim 1 further including the step of oxidizing the recovered microspheres to convert the aldehyde groups to carboxyl groups.

20. A method according to claim 1 further including the step of reacting the recovered microspheres with a compound of the formula:

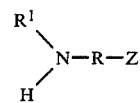

where $R^1$ is hydrogen or a hydrocarbon group, R Z is hydroxyl or R is selected from aliphatic or aromatic and Z is amine, hydroxyl or carboxyl to form an adduct.

21. A method according to claim 1 further including the step of further reacting the adduct with a material reactive with Z to form a further adduct.

* * * * *